United States Patent [19]

Liu

[11] Patent Number: 4,891,455

[45] Date of Patent: Jan. 2, 1990

[54] PROCESS FOR PREPARING MONOHALOGENATED CYCLOBUTARENES

[75] Inventor: Ming-Biann Liu, Clayton, Calif.

[73] Assignee: The Dow Chemical Company, Midland, Mich.

[21] Appl. No.: 207,802

[22] Filed: Jun. 17, 1988

Related U.S. Application Data

[63] Continuation-in-part of Ser. No. 64,714, Jun. 22, 1987, Pat. No. 4,822,930.

[51] Int. Cl.$^4$ .................. C07C 21/24; C07C 17/00
[52] U.S. Cl. .................................. 570/206; 570/207; 570/208; 570/209; 570/210
[58] Field of Search .................. 570/206, 207, 208

[56] References Cited

U.S. PATENT DOCUMENTS 4,540,011  2/1986  So .
4,540,763  9/1985  Kirchhoff .................. 526/281

OTHER PUBLICATIONS

J. B. F. Lloyd et al., "The Electrophilic Substitution of Benzocyclobutene–II", Tetrahedron, 1965, vol. 21, pp. 245-254.

Primary Examiner—Werren B. Lone

[57] ABSTRACT

Monohalogenated cyclobutarenes are prepared by halogenating a cyclobutarene in the presence of an organic complexing agent, an acid scavenger, or water. Faster reaction rates highly selective to monohalogenated cyclobutarenes are obtained without conventional heavy metal or halogen catalysts.

34 Claims, No Drawings

PROCESS FOR PREPARING MONOHALOGENATED CYCLOBUTARENES

CROSS-REFERENCE TO RELATED APPLICATION

This is a continuation-in-part of Application Ser. No. 064,714, filed June 22, 1987.

BACKGROUND OF THE INVENTION

This invention relates to a process for preparing halogenated organic compounds. More specifically, it relates to a process for preparing monohalogenated cyclobutarenes.

Monohalogenated cyclobutarenes are intermediates for the preparation of high performance monomeric and polymeric compositions for the electronics and aerospace industries. U.S. Pat. No. 4,540,763 discloses that monobrominated cyclobutarenes can be processed to prepare poly(cyclobutarene) polymeric compositions. These compositions possess thermal stability at high temperatures, as well as chemical resistance and low sensibility to water.

Processes for preparing monohalogenated cyclobutarenes are difficult because multiple halogenation reactions occur and the strained cyclobutane ring of the cyclobutarene is easily susceptible to ring-opening side reactions (see J. B. F. Lloyd et al., *Tetrahedron*, 20, pp. 2185–94 (1964)). U.S. Pat. No. 4,540,763 discloses a process for preparing monobrominated cyclobutarenes which involves diluting a cyolobutarene in acetic acid and then contacting the solution with pyridinium perbromide hydrobromide in the presence of a mercuric acetate catalyst. The reaction occurs over a four day period and uses approximately 300 percent excess brominating agent. J. B. F. Lloyd et al., *Tetrahedron*, 21, pp. 245–54, (1965), disclose a process for preparing monobrominated benzocyclobutene which involves diluting benzocyclobutene in a 95 percent aqueous solution of acetic acid and then contacting the solution with molecular bromine in the presence of an iodine catalyst. The yield of monobrominated benzocyclobutene is 78 percent after 48 hours. Unfortunately, both of these processes require large quantities of brominating agent to complete a very slow bromination reaction. Also, both processes require either a heavy metal catalyst or a halogen catalyst. The residual catalyst that inevitably finds its way into the final product is detrimental for electronics and aerospace industry applications. Furthermore, these catalysts create environmental problems related to their disposal.

Therefore, it would be desirable to have a process for preparing monohalogenated cyclobutarenes that does not require a halogen catalyst or a heavy metal catalyst. It would also be desirable to have a process providing a faster halogenation reaction highly selective to monohalogenated cyclobutarenes without requiring excessive quantities of halogenating agent.

SUMMARY OF THE INVENTION

This invention is a method of preparing monohalogenated cyclobutarenes consisting essentially of halogenating a cyclobutarene in the presence of an organic complexing agent, an acid scavenger, or water. Surprisingly, reaction rates faster than the rates disclosed in the prior art are achieved by the method of this invention without requiring a catalyst. In addition, the reaction is highly selective to monohalogenated cyclobutarenes and neither requires excessive quantities of halogenating agent nor creates an environmental problem related to the disposal of the catalysts.

The monohalogenated cyclobutarenes of this invention are useful as intermediates for the preparation of high performance monomeric and polymeric compositions for the electronics industry.

DETAILED DESCRIPTION OF THE INVENTION

As the term is used herein, "cyclobutarene" refers to a compound containing at least one aromatic ring to which is fused one or more cyclobutane rings or one or more substituted cyclobutane rings. An aromatic ring contains $(4N + 2)\pi$ electrons as described in Morrison and Boyd, *Organic Chemistry*, 3rd Edition, (1973). Suitable compounds containing at least one aromatic ring include benzene, naphthalene, biphenyl, binaphthyl, phenanthrene, anthracene, and diphenylbenzene. The aromatic ring of the cyclobutarene can be substituted with groups stable to the bromination reaction, including but not limited to groups such as methyl, methoxy, and acetate. Heterocyclic compounds such as pyridine and picoline are also included. Preferred compounds are benzene, naphthalene, and biphenyl. The most preferred compound containing at least one aromatic ring is benzene. Therefore, the most preferred cyclobutarene is benzocyclobutene.

As disclosed in U.S. Pat. No. 4,570,011, cyclobutarenes useful in this invention can be prepared by dissolving an ortho alkyl halomethyl aromatic hydrocarbon, such as ortho methylchloromethylbenzene, in an inert solvent, and then pyrolyzing the solution under suitable reaction conditions.

"Halogenating" refers to the introduction of a halogen into an organic compound by treating the compound with a halogenating agent. Suitable halogenating agents useful in this invention are those compounds which are capable of reacting with the aromatic ring of the cyclobutarene to break the carbon-hydrogen bond and to form a carbon-halogen bond under the reaction conditions Halogenating agents useful for halogenating cyclobutarenes are disclosed in H. P. Braendlin et al., *Friedel-Crafts and Related Reactions*, Vol. III, Chapter 46, pp. 1517–1593, John Wiley & Sons, New York (1964): Wagner et al., *Synthetic Organic Chemistry*, pp. 98–147, John Wiley & Sons, New York (1965); and March, *Advanced Organic Chemistry*, 3rd ed., pp. 476–479, John Wiley & Sons, New York (1985). Each of these references is incorporated by reference herein. Preferred halogenating agents are brominating and chlorinating agents. The most preferred halogenating agent is a brominating agent.

The brominating agents that can be employed in this invention can include molecular bromine, bromine chloride, pyridinium perbromide hydrobromide, dioxane dibromide, and N-bromosuccinimide. Preferred brominating agents include molecular bromine and bromine chloride. The most preferred brominating agent is molecular bromine.

Preferred chlorinating agents include molecular chlorine, N-chlorosuccinimide, and t-butyl hypochlorite. Preferred iodinating agents include molecular iodine and iodine monochloride.

The monohalogenated cyclobutarenes useful in this invention are prepared by halogenating a cyclobutarene. The term "monohalogenated" refers to the replacement of one hydrogen atom on the aromatic ring with one halogen atom. The products produced from the halogenation of the cyolobutarene include not only the monohalogenated cyclobutarene but also small quantities of hydrogen halide, unreacted halogenating agent and undesirable side reaction products. The hydrogen halide can either dissolve in the reaction mixture or evolve from the reaction mixture as a gas.

The organic complexing agents that improve the selectivity of the reaction to monohalogenated cyclobutarenes are organic compounds that will donate electrons to form donor-acceptor adducts with the unreacted halogenating agent and the hydrogen halide produced during the reaction. The adduct formed reduces the reactivity of the halogenating agent and hydrogen halide with the cyclobutane ring of the cyclobutarene and therefore reduces formation of undesirable side products A. J. Downs et al., *Comprehensive Inorganic Chemistry*, Chapter 26, pp. 1196–1197 and pp. 1201–1209, New York, N.Y., (1973), discuss the crystalline structure of halogen adducts based on X-ray diffraction studies. They describe organic compounds which form halogen adducts and the factors influencing their stability. They also describe the relative capacities of organic compounds to donate electrons. Preferably, the organic complexing agent has an electron donor capacity equal to or slightly greater than the electron donor capacity of the cyclobutarene.

Suitable organic complexing agents include aliphatic alcohols and diols having less than 10 carbon atoms, such as methanol, isobutyl alcohol, and ethylene glycol: aliphatic polymeric diols having an average molecular weight ranging from about 100 to about 15,000, such as the commercial grades of polyethylene glycol and polypropylene glycol: saturated aliphatic ethers having less than 10 carbon atoms, such as ethylene glycol ethyl ether and tripropylene glycol methyl ether; saturated cyclic ethers such as dioxane and 12-crown-4 ether: saturated aliphatic carboxylic acids and their anhydrides having less than 10 carbon atoms, such as acetic acid and acetic anhydride; other complexing agents such as dimethyl formamide and dimethyl sulfoxide: and mixtures of these organic complexing agents. Preferred organic complexing agents are methanol and ethylene glycol ethyl ether. The most preferred organic complexing agent is methanol.

Other organic complexing agents that improve the selectivity of the reaction to monohalogenated cyclobutarenes include saturated quaternary ammonium salts, such as tetraalkylammonium salts and trialkylamine salts. Although these compounds do not donate electrons to form donor-acceptor adducts, their effectiveness as complexing agents has been demonstrated.

The *Dictionary of Scientific and Technical Terms*, McGraw-Hill, Second Edition (1978) defines a scavenger as "a substance added to a mixture or other system to remove or inactivate impurities". Acid scavengers useful in this invention remove or inactivate hydrogen halide produced during the halogenation by reacting with the hydrogen halide to form a side product. The scavenger does not react with the cyclobutarene. Preferably, the scavenger reacts readily with hydrogen halide but does not react readily with the halogenating agent to prevent the halogenation of the cyolobutarene. The acid scavenger can be organic or inorganic.

Suitable organic acid scavengers include epoxides having less than 10 carbon atoms, such as ethylene oxide, propylene oxide, epichlorohydrin, and epibromohydrin: aliphatic tertiary alcohols having less than 10 carbon atoms, such as tertiary butyl alcohol: aliphatic primary, secondary and tertiary amines, such as ethylamine, diethylamine, and triethylamine; heterocyclic compounds such as pyridine and picoline, and triarylphosphines such as triphenylphosphine. The preferred scavengers are the epoxides having less than 10 carbon atoms and the tertiary amines. The most preferred epoxide is epichlorohydrin and the most preferred tertiary amine is triethylamine.

Suitable inorganic acid scavengers include alkali metal and alkali earth metal salts of alcohols and carboxylic acids, such as sodium methylate, sodium ethylate, and sodium acetate: alkali metal and alkali earth metal bases, such as sodium hydroxide and calcium hydroxide; and carbonates and bicarbonates of alkali metal and alkali earth metals, such as sodium bicarbonate and potassium carbonate.

When the cyolobutarene is halogenated in the presence of water, the water acts in a manner similar to that of the organic complexing agent by forming donor-acceptor adducts with the unreacted halogenating agent and the hydrogen halide.

In a preferred embodiment of this invention, the solubility of hydrogen halide produced during halogenation in the reaction mixture is reduced. The reduced solubility will increase the quantity of hydrogen halide that will evolve from the reaction mixture as a gas. Since more hydrogen halide will evolve from the reaction mixture as a gas, there will be less hydrogen halide in the reaction mixture that can react with the cyclobutane ring of the cyclobutarene to produce undesirable side products. Therefore, an increased selectivity of monohalogenated cyclobutarene will result.

One method of reducing the solubility of hydrogen halide in the reaction mixture is to dilute the cyclobutarene in an appropriate nonreacting diluent before halogenation. Appropriate diluents are those in which the solubility of hydrogen halide is low. Ahmed et al., *Journal of Applied Chemistry*, 20., pp. 109–116, (April 1970), disclose the solubilities of hydrogen halides in various diluents. Suitable diluents that can be employed in this invention include methylene chloride, chloroform, carbon tetrachloride, ethylene dichloride, bromochloromethane, and hexane. The preferred diluents are methylene chloride, chloroform, and bromochloromethane. The most preferred diluent is methylene chloride.

Certain organic complexing agents can also act as appropriate nonreacting diluents. Examples of such organic complexing agents include acetic acid, methanol, and water.

The mole ratio of the cyclobutarene to the complexing agent or water employed in the practice of this invention can range from about 0.001:1 to about 100:1. A more preferable range is from about 0.005:1 to about 70:1. The most preferable range is from about 0.05:1 to about 6.0:1. The mole ratio of the cyclobutarene to the scavenger employed in the practice of this invention can range from about 0.1:1 to about 100:1. A more preferable range is from about 0.3:1 to about 20:1. The most preferable range is from about 0.5:1 to about 2.0:1.

If a diluent is employed to dilute the cyclobutarene before halogenation, the weight ratio of the diluent to the cyclobutarene can range from about 0 1:1 to about 100:1. A more preferable range is from about 0.5:1 to about 20:1. The mole ratio of the halogenating agent to the cyclobutarene can range from about 0.1:1 to about 2.0:1. A more preferable range is from about 0.90:1 to about 1.10:1.

The operating temperature and pressure of the reaction system are limited solely by practical considerations. The temperature can range from the freezing point to the boiling point of the reaction mixture. Preferably, the operating temperature ranges from about 25° C. to about 60° C. Although the halogenation reaction will proceed at both high and low operating pressures, it is preferable to run as close to atmospheric pressure as possible because higher pressures will increase the solubility of the hydrogen halide in the reaction system and therefore generate more side reactions. Also, high operating pressures necessitate the use of more expensive pressure rated equipment.

In a preferred embodiment of this invention, the halogenating agent is added continuously or periodically to the reaction mixture to control the evolution of gaseous hydrogen halide. By controlling the evolution of the gaseous hydrogen halide, the operating pressure of the system can be maintained as close to atmospheric pressure as possible.

The halogenation reaction proceeds almost instantaneously when the halogenating agent contacts the cyclobutarene. In most instances, the required reaction time depends on the rate of addition of the halogenating agent to the reaction system. The rate of addition of the halogenating agent depends on the ability of the system to remove the gaseous hydrogen halide and the design pressure of the reactor.

The selectivity of the reaction to monohalogenated cyclobutarenes decreases with conversion because the monohalogenated cyclobutarenes prepared from the halogenation can react further with the reaction mixture to form undesirable side products. Advantageously, the monohalogenated cyclobutarenes are separated quickly from the reaction mixture. In preferred embodiments of this invention, the selectivity will range from about 75 mole percent to about 95 mole percent. Selectivity is defined as the mole percentage of the reacted cyclobutarene that forms monohalogenated cyclobutarenes.

After the halogenation reaction, the monohalogenated cyclobutarenes can easily be separated from the side products produced by the reaction. One method of separation is to fractionally distill all of the impurities from the reaction system. Another method of separation involves adding an aqueous solution of a reducing agent, such as sodium metabisulfite, to neutralize the residual halogenating agent and to extract the hydrogen halide from the organic phase of the reaction mixture to the aqueous phase. The aqueous phase can then be physically separated from the organic phase and then the organic phase can be fractionally distilled to recover the monohalogenated cyclobutarenes. Preferably, the recovered monohalogenated cyclobutarenes have a purity of at least 97 percent by weight.

The recovered monohalogenated cyclobutarenes are useful intermediates which can be processed to prepare poly(cyclobutarene) monomeric and polymeric compositions. U.S. Pat. No. 4,540,763 discloses methods of preparing these compositions from monobrominated cyclobutarenes. The polymeric compositions have excellent thermal stability at high temperatures, good chemical resistance to most industrial solvents, and a low sensitivity to water. These properties are highly desirable for applications in the electronics and aerospace industries. The following examples are illustrative and are not intended to limit the scope of this invention. All percentages are mole percent unless otherwise indicated.

EXAMPLES

EXAMPLE 1

2005 grams (g) Benzocyclobutene (19.25 moles), 2000 g methylene chloride (23.55 moles) and 200 g methanol (6.24 moles) are charged to a jacketed, 8 liter cylindrical 3-neck round bottom reactor equipped with a mechanical stirrer, a digital thermocouple, and a reflux condenser connected to a caustic scrubber. The mixture is heated to 40° C. by recirculating an aqueous solution of ethylene glycol from a constant temperature bath through the jacket. 3275 g Bromine (20.49 moles) are fed to the reactor at a constant flow rate of 728 g/hr. During the addition, the temperature increases to a range between 48° C. and 57.5° C. and reflux is observed. A sample of the reaction mixture is taken each hour for 4 hours. Another sample is taken after 4 hours and 30 minutes when all of the bromine has been fed to the reactor. The residual bromine of each sample is neutralized with the requisite amount of an aqueous solution of sodium metabisulfite. Each organic layer is separated and analyzed using a capillary gas chromatograph to determine its composition. A final sample of the reaction mixture is taken after 5 hours and 30 minutes. It is washed with aqueous sodium metabisulfite and the organic layer is separated and analyzed in a similar manner. The analysis of each sample is shown in Table I.

TABLE I

| Reaction Time (Hours) | Unreacted Benzocyclobutene (Percent) | Monobrominated Benzocyclobutenes (Percent) | 2-Bromophenethyl Bromide (Percent) | Multi-brominated Benzocyclobutene (Percent) | Phenethyl Bromide (Percent) | Selectivity (Percent) |
|---|---|---|---|---|---|---|
| 1.0 | 84.9 | 13.7 | 1.5 | 0 | 0 | 91 |
| 2.0 | 58.4 | 36.9 | 4.6 | 0 | 0 | 89 |
| 3.0 | 38.1 | 54.7 | 6.7 | 0.2 | 0.2 | 88 |
| 4.0 | 19.2 | 70.1 | 8.9 | 1.1 | 0.6 | 87 |
| 4.5* | 10.0 | 77.0 | 10.2 | 1.9 | 0.9 | 86 |
| 5.5 | 4.4 | 81.0 | 10.9 | 2.7 | 1.1 | 85 |

Table I indicates that a significantly improved selectivity of the reaction to monobrominated benzocyclobutenes is obtained by the method of this invention without the use of the catalysts of the prior art. Table I also indicates high selectivities are achieved at much faster reaction rates than the rates achieved by the prior art.

EXAMPLE 2

100.95 g Benzocyclobutene (0.969 moles), 115.52 g methylene chloride (1.36 moles) and 6.00 g methanol (0.187 moles) are charged to the same reactor as that of Example 1 equipped with a 500 ml dropping funnel. The mixture is heated to 40° C. 163.4 g Bromine (1.022 moles) are added dropwise to the reaction mixture through the dropping funnel. During the addition, the temperature increases to 44.2° C. and reflux is observed. After 78 minutes the addition of bromine is completed. After 16 hours, the residual bromine of the reaction mixture is neutralized with 200 ml of an aqueous solution containing 10 g of sodium metabisulfite. The organic layer is separated and analyzed using a capillary gas chromatograph. The analysis indicates that the product contains 3.7 percent unreacted benzocyclobutene, 81.2 percent monobrominated benzocyclobutenes, 6.5 percent 2-bromophenethylbromide, 8.4 percent multibrominated benzocyclobutenes and less than 0.3 percent phenethyl bromide.

EXAMPLE 3

1.6 g Bromine (104 percent theoretical) are added to a solution containing 1 g benzocyclobutene and 0.1 g methanol at room temperature. After 12 hours a sample of the reaction mixture is washed with aqueous sodium metabisulfite. The organic layer is separated and analyzed using a capillary gas chromatograph. The analysis indicates that the product contains 24.8 percent benzocyclobutene, 56.5 percent monobrominated benzocyclobutenes, 9.1 percent 2-bromophenethyl bromide, 9.3 percent multibrominated benzocyclobutenes, and 0.3 percent phenethyl bromide.

EXAMPLE 4

In each of a series of runs, 1.6 g bromine are added to a solution containing 4 g methylene chloride, 1 g benzocyclobutene and 0.1 g of one of several selected complexing agents (or water) at room temperature. After 12 hours a sample of the reaction mixture is washed with aqueous sodium metabisulfite. The organic layer is separated and analyzed using a capillary gas chromatograph to determine the percent conversion and the percent selectivity. The conversion and selectivity are compared to a first run in which neither the complexing agent (or water) nor methylene chloride are added and a second run in which the complexing agent (or water) is not added. Percent conversion is defined as the mole percentage of benzocyclobutene that reacts. The results are shown in Table II.

TABLE II

| Complexing Agent (or Water) | Diluent | Conversion (Percent) | Selectivity (Percent) |
|---|---|---|---|
| None* | None | 92.3 | 71 |
| None* | Methylene chloride | 83.1 | 76 |
| Methanol | Methylene chloride | 96.0 | 86 |
| Water | Methylene chloride | 90.3 | 81 |
| Ethyl Glycol Ethyl Ether | Methylene chloride | 87.7 | 87 |
| Glacial Acetic Acid | Methylene chloride | 94.5 | 81 |
| Tetra(n-butyl) Ammonium Hydrogen Sulfate | Methylene Chloride | 92.8 | 83 |

*Not an embodiment of this invention.

Table II indicates that a high selectivity of the reaction to monobrominated benzocyclobutenes is obtained by the method of the present invention using various complexing agents or water. The selectivities of the two runs obtained without the complexing agent (or water) are poor relative to the selectivities obtained according to the present invention.

EXAMPLE 5

1.6 g Bromine are added to a solution containing 1 g benzocyclobutene and 4 g of methanol at room temperature. After 12 hours, a sample of the reaction mixture is washed with aqueous sodium metabisulfite. The organic layer is separated and analyzed using a capillary gas chromatograph to determine the percent conversion and the percent selectivity. The experiment is repeated replacing the 4 g of methanol with 4 g of water. The results are shown in Table III.

TABLE III

| Complexing Agent (or Water) | Diluent | Conversion (Percent) | Selectivity (Percent) |
|---|---|---|---|
| Methanol | None | 50.5 | 85 |
| Water | None | 92.0 | 81 |

Table III indicates that a high selectivity of the reaction to monobrominated benzocyclobutenes is obtained without the use of a diluent.

EXAMPLE 6

The procedure of Example 4 is followed, except that the methylene chloride diluent is replaced with various diluents listed in Table IV and the complexing agent employed is methanol. The results are shown in Table IV.

TABLE IV

| Complexing Agent | Diluent | Conversion (Percent) | Selectivity (Percent) |
|---|---|---|---|
| Methanol | 95 percent Acetic Acid | 73.0 | 82 |
| Methanol | Chloroform | 88.2 | 86 |
| Methanol | Carbon Tetrachloride | 82.5 | 80 |
| Methanol | Ethylene Dichloride | 94.9 | 81 |
| Methanol | Bromochloromethane | 87.7 | 84 |
| Methanol | Hexane | 80.9 | 81 |
| Methanol | Water | 83.0 | 77 |

Table IV indicates that a high selectivity of the reaction to monobrominated benzocyclobutenes is still obtained using various diluents other than methylene chloride.

EXAMPLE 7

The procedure of Example 4 is followed, except that the complexing agents (or water) are replaced with various scavengers listed in Table V. The results are shown in Table V.

TABLE V

| Scavenger | Molar ratio of Scavenger to Benzocyclobutene | Diluent | Conversion (Percent) | Selectivity (Percent) |
|---|---|---|---|---|
| T-Butyl Alcohol | 0.14 | Methylene chloride | 75.6 | 78 |
| Epichlorohydrin | 1.0 | Methylene Chloride | 85.1 | 80 |
| Triethyl- | 0.10 | Methylene | 78.8 | 85 |

TABLE V-continued

| Scavenger | Molar ratio of Scavenger to Benzo-cyclo-butene | Diluent | Conversion (Percent) | Selectivity (Percent) |
|---|---|---|---|---|
| amine Sodium Methylate | 1.0 | Chloride Methylene Chloride | 44.8 | 80 |

Table V indicates that a high selectivity of the reaction to monobrominated benzocyclobutenes is obtained by the method of the present invention using various scavengers instead of complexing agents or water.

What is claimed is:

1. A method of preparing monohalogenated cyclobutarenes consisting essentially of halogenating a cyclobutarene with a halogenating agent in the presence of an organic complexing agent, an acid scavenger, or water.

2. The method of claim 1 wherein the halogenating agent is a brominating agent or a chlorinating agent.

3. The method of claim 2 wherein the halogenating agent is a brominating agent.

4. The method of claim 3 wherein the cyclobutarene is benzocyclobutene.

5. The method of claim 4 wherein the chlorinating agent is selected from the group consisting of molecular chlorine, N-chlorosuccinimide and t-butyl hypochlorite.

6. The method of claim 5 wherein the chlorinating agent is molecular chlorine.

7. The method of claim 1 wherein the cyclobutarene is diluted in an appropriate nonreacting diluent.

8. The method of claim 7 wherein the diluent is selected from the group consisting of methylene chloride, ethylene dichloride, chloroform, carbon tetrachloride, bromochloromethane, hexane, acetic acid, methanol, and water.

9. The method of claim 8 wherein the diluent is methylene chloride.

10. The method of claim 1 wherein the organic complexing agent has an electron donor capacity equal to or slightly greater than the electron donor capacity of the cyclobutarene.

11. The method of claim 10 wherein the organic complexing agent is selected from the group consisting of saturated aliphatic alcohols and diols having less than 10 carbon atoms; aliphatic polymeric diols having an average molecular weight ranging from about 100 to about 15,000; saturated aliphatic ethers having less than 10 carbon atoms; saturated cyclic ethers: saturated quaternary ammonium salts: saturated carboxylic acids and their anhydrides having less than 10 carbon atoms; dimethyl formamide; dimethyl sulfoxide: and mixtures of these complexing agents.

12. The method of claim 11 wherein the organic complexing agent is selected from the group consisting of saturated aliphatic alcohols and diols having less than 10 carbon atoms: aliphatic polymeric diols having an average molecular weight ranging from about 100 to about 15,000: saturated aliphatic ethers having less than 10 carbon atoms; saturated cyclic ethers; and saturated quaternary ammonium salts.

13. The method of claim 11 wherein the organic complexing agent is selected from the group consisting of saturated aliphatic alcohols and diols having less than 10 carbon atoms: aliphatic polymeric diols having an average molecular weight ranging from about 100 to about 15,000: saturated aliphatic ethers having less than 10 carbon atoms: and saturated cyclic ethers.

14. The method of claim 11 wherein the organic complexing agent is selected from the group consisting of saturated aliphatic alcohols and diols having less than 10 carbon atoms; aliphatic polymeric diols having an average molecular weight ranging from about 100 to about 15,000; and saturated aliphatic ethers having less than 10 carbon atoms.

15. The method of claim 11 wherein the organic complexing agent is selected from the group consisting of saturated aliphatic alcohols and diols having less than 10 carbon atoms, and saturated aliphatic ethers having less than 10 carbon atoms.

16. The method of claim 15 wherein the organic complexing agent is selected from the group consisting of methanol and ethylene glycol ethyl ether.

17. The method of claim 16 wherein the organic complexing agent is methanol.

18. The method of claim 6 wherein the mole ratio of the cyclobutarene to the organic complexing agent or water ranges from about 0.05:1 to about 4.0:1.

19. The method of claim 1 wherein the acid scavenger reacts readily with hydrogen halide but does not react readily with the halogenating agent.

20. The method of claim 6 wherein the acid scavenger is organic.

21. The method of claim 20 wherein the organic acid scavenger is selected from the group consisting of epoxides having less than 10 carbon atoms; aliphatic tertiary alcohols having less than 10 carbon atoms: alkali metal and alkali earth metal salts of aliphatic alcohols having less than 10 carbon atoms: aliphatic primary, secondary, and tertiary amines: heterocyclic compounds: and triarylphosphines.

22. The method of claim 21 wherein the organic acid scavenger is selected from the group consisting of epoxides having less than 10 carbon atoms and tertiary amines.

23. The method of claim 22 wherein the organic acid scavenger is selected from the group consisting of epichlorohydrin and triethylamine.

24. The method of claim 1 wherein the acid scavenger is inorganic.

25. The method of claim 24 wherein the inorganic acid scavenger is selected from the group consisting of alkali metal and alkali earth metal salts of alcohols and carboxylic acids, alkali metal and alkali earth metal bases, and carbonates and bicarbonates of alkali metal and alkali earth metals.

26. The method of claim 25 wherein the inorganic acid scavenger is sodium methylate.

27. The method of claim 1 wherein the mole ratio of the cyclobutarene to the acid scavenger ranges from about 0.5:1 to about 2.0:1.

28. The method of claim 1 wherein the weight ratio of diluent to the cyclobutarene ranges from about 0.5:1 to about 20:1.

29. The method of claim 1 wherein the mole ratio of the halogenating agent to the cyclobutarene ranges from about 0.90:1 to about 1.10:1.

30. The method of claim 1 wherein the selectivity of the reaction to monohalogenated cyclobutarenes ranges from about 75 mole percent to about 95 mole percent.

31. The method of claim 1 wherein the halogenation reaction is maintained at atmospheric pressure.

32. The method of claim 31 wherein the halogenating agent is added continuously or periodically during the bromination step.

33. The method of claim 32 wherein the temperature is maintained in the range of about 25° C. to about 60° C.

34. The method of claim 1 wherein the mole ratio of the cyclobutarene to the complexing agent or water ranges from about 0.05:1 to about 6.0:1.

* * * * *